United States Patent [19]

Tomiyama et al.

[11] 4,407,816

[45] Oct. 4, 1983

[54] 3-SUBSTITUTED-2-PROPENIMIDAMIDES AND METHOD OF MANUFACTURING THE SAME

[75] Inventors: Tsuyoshi Tomiyama, Sakaki; Akira Tomiyama, Togura, both of Japan

[73] Assignee: Kotobuki Seiyaku Company Limited, Nagano, Japan

[21] Appl. No.: 289,903

[22] Filed: Aug. 4, 1981

[30] Foreign Application Priority Data

Aug. 8, 1980 [JP] Japan .................................. 55-109060
Nov. 1, 1980 [JP] Japan .................................. 55-154348

[51] Int. Cl.$^3$ ..................... A61K 31/38; A61K 31/34; A61K 31/275; A61K 31/165
[52] U.S. Cl. .................................. 424/275; 424/285; 424/304; 424/324; 549/74; 549/75; 549/76; 549/491; 549/496; 260/453 AR; 564/47; 564/105
[58] Field of Search ..................... 549/74, 75, 76, 491, 549/496; 260/453 AR; 564/47, 105; 424/275, 285, 304, 324

[56] References Cited

U.S. PATENT DOCUMENTS 4,252,819  2/1981  Hirata et al. .......................... 549/76

*Primary Examiner*—A. Siegel
*Attorney, Agent, or Firm*—Robert E. Burns; Emmanuel J. Lobato; Bruce L. Adams

[57] ABSTRACT

New derivatives of 3-furyl-, 3-thienyl- and 3-phenyl-2-propenimidamides are disclosed, which are useful as anti-ulcer agents. These new compounds are synthesized by reacting an imino ether derived from a corresponding 3-substituted-2-propenenitrile with a suitable amine.

13 Claims, No Drawings

3-SUBSTITUTED-2-PROPENIMIDAMIDES AND METHOD OF MANUFACTURING THE SAME

BACKGROUND OF THE INVENTION

This invention relates to new 3-substituted 2-propenimidamide derivatives, which may also be referred to as 3-substituted-propenamidines, the method of manufacturing the same, therapeutic compositions containing these compounds and therapeutic uses thereof. More specifically the invention concerns N'-cyano and N'-carbamoyl derivatives of 3-furyl-, 3-thienyl- and 3-phenylpropenimidamides, pharmaceutical compositions containing these compounds and a method of treating peptic ulcers therewith.

SUMMARY OF THE INVENTION

The principal object of the present invention is the provision of novel compounds having advantageous pharmaceutical properties.

Another object of the present invention is the provision of pharmaceutical compositions useful as anti-peptic ulcerative agents.

Still another object of the present invention is the provision of a new method of treating peptic ulcer.

Further important objects of the present invention are the provisions of 3-substituted-2-propenimidamides and a method for the manufacture thereof.

These and other objects of the invention will become apparent from the description that follows.

The new compounds of the invention have the formula:

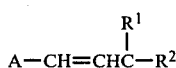  I wherein:
A is a furyl, thienyl, phenyl, chlorophenyl or lower-alkoxy-phenyl group;
$R^1$ represents =NCN or =N—CONH$_2$ and
$R^2$ represents —NHR$^3$ or —NHNHCOR$^4$, wherein $R^3$ is a hydrogen atom, or a lower-alkyl, phen-lower-alkyl or cyclohexyl group, said cyclohexyl group being optionally substituted by lower-alkyl and $R^4$ is a lower-alkyl group, and
pharmaceutically acceptable acid addition salts thereof.

Compounds of the invention inhibit gastric secretion and therefore a pharmaceutical composition containing at least one compound of formula I is useful in the treatment of peptic ulcers.

Compounds of formula I may be prepared by the reaction of cyanamide with an imidate of the formula

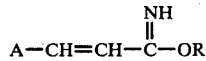  III wherein A is as defined in formula I and R is an alkyl group, to form an N'-cyano-2-propenimidate of the formula

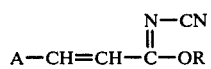  IV and then reacting the N'-cyano-2-propenimidate with an amine or hydrazide of the formula H$_2$NR$^3$ or H$_2$NNHCOR$^4$, wherein R$^3$ and R$^4$ are as defined in formula I.

DESCRIPTION OF THE INVENTION

The compounds of the invention represented by formula I are N'-cyano- or N'-carbamoyl-3-substituted-2-propenimidamides which may also be referred to as corresponding 2-propenamidines and pharmaceutically acceptable acid addition salts thereof, which may contain lower-alkyl, phen-lower-alkyl, cyclohexyl optionally substituted with lower-alkyl or an alkanoylamino substituent on the amido group. Preferable substituents on the amido group include methyl, ethyl, propyl, isopropyl, n-butyl, isobutyl, phenethyl, cyclohexyl, methylcyclohexyl, ethylcyclohexyl, and propionylamido.

The term "lower alkyl" as used herein designates alkyl groups which contain from 1 to 4 carbon atoms.

Two isomers, the trans isomer designated by E and the cis isomer designated by Z exist for each compound of formula I.

Pharmaceutically acceptable acid addition salts of the compounds of formula I are included in this invention, preferred acid addition salts include salts of hydrochloric, hydrobromic, sulfuric, fumaric, maleic and succinic acid and may be conveniently formed from the corresponding base by standard procedure.

The following compounds of the invention are of particular interest.

(1) N'-cyano-3-(2-thienyl)-2-propenimidamide
(2) N'-cyano-3-(2-furyl)-2-propenimidamide
(3) N-methyl-N'-cyano-3-(2-thienyl)-2-propenimidamide
(4) N-n-propyl-N'-cyano-3-(2-furyl)-2-propenimidamide
(5) N-isopropyl-N'-cyano-3-(2-thienyl)-2-propenimidamide
(6) N-ethyl-N'-cyano-3-(2-furyl)-2-propenimidamide
(7) N-n-butyl-N'-cyano-3-(2-furyl)-2-propenimidamide
(8) N-cyclohexyl-N'-cyano-3-(2-furyl)-2-propenimidamide
(9) N-(4-methylcyclohexyl)-N'-cyano-3-(2-furyl)-2-propenimidamide
(10) N-propionylamino-N'-cyano-3-(2-furyl)-2-propenimidamide
(11) N-n-propyl-N'-cyano-3-phenyl-2-propenimidamide
(12) N-n-butyl-N'-cyano-3-phenyl-2-propenimidamide
(13) N-isopropyl-N'-cyano-3-phenyl-2-propenimidamide
(14) N-ethyl-N'-cyano-3-phenyl-2-propenimidamide
(15) N-isobutyl-N'-cyano-3-phenyl-2-propenimidamide
(16) N-cyclohexyl-N'-cyano-3-phenyl-2-propenimidamide
(17) N-(3-methylcyclohexyl)-N'-cyano-3-(2-furyl)-2-propenimidamide
(18) N-phenethyl-N'-cyano-3-(2-furyl)-2-propenimidamide
(19) N-isopropyl-N'-cyano-3-(2-furyl)-2-propenimidamide
(20) N-methyl-N'-cyano-3-phenyl-2-propenimidamide
(21) N'-cyano-3-(2-furyl)-2(E)-propenimidamide
(22) N-isopropyl-N'-cyano-3-(2-furyl)-2(E)-propenimidamide

(23) N-(3-methylcyclohexyl)-N'-cyano-3-phenyl-2-propenimidamide
(24) N-(4-methylcyclohexyl)-N'-cyano-3-phenyl-2-propenimidamide
(25) N-methyl-N'-cyano-3-phenyl-2-propenimidamide
(26) N'-carbamoyl-3-(2-furyl)-2-propenimidamide hydrochloride
(27) N-n-propyl-N'-carbamoyl-3-phenyl-2-propenimidamide hydrochloride
(28) N-n-butyl-N'-carbamoyl-3-phenyl-2-propenimidamide hydrochloride
(29) N-isopropyl-N'-carbamoyl-3-phenyl-2-propenimidamide hydrochloride
(30) N-cyclohexyl-N'-carbamoyl-3-phenyl-2-propenimidamide hydrochloride
(31) N-methyl-N'-carbamoyl-3-phenyl-2-propenimidamide hydrochloride
(32) N-(3-methylcyclohexyl)-N'-carbamoyl-3-phenyl-2-propenimidamide hydrochloride
(33) N-(4-methylcyclohexyl)-N'-carbamoyl-3-phenyl-2-propenimidamide hydrochloride
(34) N-(4-methylcyclohexyl)-N'-carbamoyl-3-(2-furyl)-2-propenimidamide hydrochloride.
(35) N-isopropyl-N'-carbamoyl-3-(2-furyl)-2-propenimidamide hydrochloride
(36) N-methyl-N'-cyano-3-(o-chlorophenyl)-2-propenimidamide
(37) N-ethyl-N'-cyano-3-(o-chlorophenyl)-2-propenimidamide
(38) N-n-propyl-N'-cyano-3-(o-chlorophenyl)-2-propenimidamide
(39) N-isobutyl-N'-cyano-3-(o-chlorophenyl)-2-propenimidamide
(40) N-cyclohexyl-N'-cyano-3-(o-chlorophenyl)-2-propenimidamide
(41) N-(4-methylcyclohexyl)-N'-cyano-3-(o-chlorophenyl)-2-propenimidamide
(42) N-isopropyl-N'-cyano-3-(o-chlorophenyl)-2-propenimidamide
(43) N-ethyl-N'-cyano-3-(p-chlorophenyl)-2-propenimidamide
(44) N-isopropyl-N'-cyano-3-(p-chlorophenyl)-2-propenimidamide
(45) N-n-propyl-N'-cyano-3-(p-chlorophenyl)-2-propenimidamide
(46) N-isobutyl-N'-cyano-3-(p-chlorophenyl)-2-propenimidamide
(47) N-cyclohexyl-N'-cyano-3-(p-chlorophenyl)-2-propenimidamide
(48) N-(4-methylcyclohexyl)-N'-cyano-3-(p-chlorophenyl)-2-propenimidamide
(49) N-methyl-N'-cyano-3-(p-methoxyphenyl)-2-propenimidamide
(50) N-ethyl-N'-cyano-3-(p-methoxyphenyl)-2-propenimidamide
(51) N-n-propyl-N'-cyano-3-(p-methoxyphenyl)-2-propenimidamide
(52) N-isobutyl-N'-cyano-3-(p-methoxyphenyl)-2-propenimidamide
(53) N-isobutyl-N'-cyano-3-(p-methoxyphenyl)-2-propenimidamide
(54) N-cyclohexyl-N'-cyano-3-(p-methoxyphenyl)-2-propenimidamide
(55) N-(4-methylcyclohexyl)-N'-cyano-3-(p-methoxyphenyl)-2-propenimidamide
(56) N-isopropyl-N'-carbamoyl-3-(o-chlorophenyl)-2-propenimidamide hydrochloride
(57) N-methyl-N'-carbamoyl-3-(o-chlorophenyl)-2-propenimidamide hydrochloride
(58) N-ethyl-N'-carbamoyl-3-(o-chlorophenyl)-2-propenimidamide hydrochloride
(59) N-cyclohexyl-N'-carbamoyl-3-(o-chlorophenyl)-2-propenimidamide hydrochloride
(60) N-n-propyl-N'-carbamoyl-3-(o-chlorophenyl)-2-propenimidamide hydrochloride
(61) N-(4-methylcyclohexyl)-N'-carbamoyl-3-(o-chlorophenyl)-2-propenimidamide hydrochloride.
(62) N-isopropyl-N'-carbamoyl-3-(p-chlorophenyl)-2-propenimidamide hydrochloride
(63) N-cyclohexyl-N'-carbamoyl-3-(p-chlorophenyl)-2-propenimidamide hydrochloride
(64) N-(4-methylcyclohexyl)-N'-carbamoyl-3-(p-chlorophenyl)-2-propenimidamide hydrochloride
(65) N-isopropyl-N'-carbamoyl-3-(p-methoxyphenyl)-2-propenimidamide hydrochloride
(66) N-cyclohexyl-N'-carbamoyl-3-(p-methoxyphenyl)-2-propenimidamide hydrochloride
(67) N-(4-methylcyclohexyl)-N'-carbamoyl-3-(p-methoxyphenyl)-2-propenimidamide hydrochloride. p The above-mentioned compounds numbered from 1 to 67, will be referred to hereinafter, as Compound 1, Compound 2, . . . Compound 67, respectively.

The new compounds of the invention of formula I may be prepared in the following manner: a 3-substituted-2-propenenitrile of the formula:

$$A-CH=CH-CN \qquad \text{II}$$

wherein A is as defined in formula I, may be converted to the imino ether of the formula $$A-CH=CH-\overset{NH}{\underset{\|}{C}}-OR \qquad \text{III}$$

wherein R represents an alkyl radical, by means of a Pinner reaction or by reaction with an alcohol in the presence of a basic catalyst according to the method of the *Journal Of Organic Chemistry* 26, p. 412, which is incorporated herein by reference. The resulting imino ether of formula III is then reacted with cyanamide in alcohol according to *Gazz. Chem. Ital.* 41 II., p. 98, 1911, which is incorporated herein by reference. Reaction of the resultant alkyl 3-substiuted-N-cyanopropenimidate of the formula $$A-CH=CH-\overset{NCN}{\underset{\|}{C}}-OR, \qquad \text{IV}$$

wherein A is as defined with respect to formula I and R is an alkyl group, with a suitable amine of the formula $H_2NR^3$ or a hydrazide of the formula $H_2NNHCOR^4$, wherein $R^3$ and $R^4$ are as defined with respect to formula I yields a N-cyano-3-substituted-2-propenimidamide of the invention of the formula:

$$A-CH=CH-\overset{NCN}{\underset{\|}{C}}-R^2 \qquad \text{V}$$

wherein $R^2$ is as defined in formula I. This reaction proceeds satisfactorily at room temperature, but if necessary or desired, the mixture can be warmed during the reaction.

By treating the compound of formula V with HCl gas in alcohol, or with concentrated hydrochloric acid, an N'-carbamoylpropenimidamide of the invention results which has the formula:

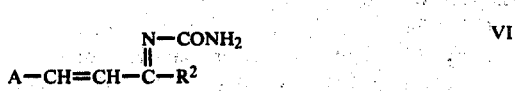

wherein $R^2$ is as defined with respect to formula I.

3-Substituted-2-propenenitrile of formula II, can be separated efficiently by distillation, column chromatography or recrystallization into respective E and Z isomers. The isomeric form is retained through the series of the above-mentioned reactions necessary to produce a compound of this invention.

The 3-substituted-2-propenimidamides of the invention possess a marked gastric antisecretory activity and the use thereof as an anti-peptic ulcerative agent in clinics is promising. These compounds can be administered in pharmaceutical preparations with the usual excipients for oral and parenteral use in preferred dosage.

The dosage of the instant compounds is about 500 mg–1500 mg. daily for an adult. The preferred dosage is 9000–1200 mg.

The following example illustrates the preparation of typical Composition of the present invention in oral dosage unit form.

| INGREDIENTS: | |
|---|---|
| Compound 9 | 150 mg. |
| Lactose | 20 mg. |
| Starch | 10 mg. |
| Magnesium Stearate | 2 mg. |

The ingredients are mixed and filled into a capsule.

In preparation of pharmaceutical compositions containing the new compounds, almost excipients of common use can be used. For example, water, edible oil, dextrin, crystal cellulose, licorice, glycose and so on are applicable.

For the better understanding of this invention, pharmacological properties and the examples of manufactural procedures the following illustrative examples are set forth; these examples are illustrative only and the invention should not be construed as being restricted thereto.

Pharmacological Determinations

Determination of the gastric antisecretory activities of the compounds were carried out by using Wistar rats according to the method described by Shay et al in *Gastroenterology* 26, 906. After 4 hours of pylorus ligation, the animals were sacrificed and their stomachs removed, the gastric juices obtained were submitted to acidity and volume (ml.) determinations. The test compounds were administered intraduodenally just after pylorus ligation. The results are summarized in Table 1. Data are shown as inhibitory % to control group.

TABLE 1

| Compound No. | Dose (mg./kg.) | Inhibitory % of gastric volume | Inhibitory % of total acid |
|---|---|---|---|
| 4 | 50 | 69.2 | 77.2 |
| 7 | 50 | 69.7 | 71.5 |
| 8 | 50 | 60.6 | 63.3 |
| 10 | 50 | 33.6 | 39.5 |

TABLE 1-continued

| Compound No. | Dose (mg./kg.) | Inhibitory % of gastric volume | Inhibitory % of total acid |
|---|---|---|---|
| 26 | 50 | 57.6 | 73.2 |
| 16 | 50 | 70.8 | 82.5 |
| 34 | 50 | 76.0 | 95.4 |
| 38 | 50 | 48.2 | 61.4 |
| 51 | 50 | 44.0 | 46.8 |
| 52 | 50 | 30.0 | 30.1 |
| 57 | 50 | 70.2 | 74.2 |
| 58 | 50 | 64.9 | 59.0 |
| 62 | 50 | 70.6 | 61.0 |
| 64 | 50 | 33.3 | 31.5 |

EXAMPLE 1

Compound 1:
N'-Cyano-3-(2-thienyl)-2-propenimidamide

Ethyl-3-(2-thienyl)-2-propenimidate HCl in an amount of 2.16 g. is added to 4 ml. of cold water and this solution is alkalinized with $K_2CO_3$ and extracted with ether. The ether layer is evaporated and the residue is dissolved in 1 ml. of ethanol. Cyanamide in an amount of 0.42 g. is added to the ethanol solution which is allowed to stand over night at room temperature. The precipitated crystals are recrystallized from ethanol:ether (1:1).

The resulting compound,

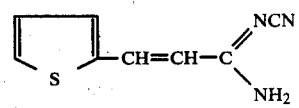

has the following characteristics:
m.p. 178° C. (decomp.)
ir. 3320, 3160, 2160, 1640, 1610, 1540 cm.$^{-1}$
M.S.: m/e 177 (M+)

EXAMPLE 2

Compound 2:
N'-Cyano-3-(2-furyl)-2-propenimidamide.

Use of ethyl 3-(2-furyl)-2-propenimidate HCl in the procedure of Example 1 yields the compound,

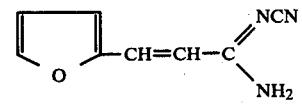

which has the following characteristics:
mp: 198° C.
ir: 3340, 3180, 2170, 1660, 1550 cm.$^{-1}$
M.S.: m/e 161 (M+)

EXAMPLE 3

Compound 3:
N-Methyl-N'-cyano-3-(2-thienyl)-2-propenimidamide.

Step A—To a solution of 1.34 g. of ethyl 3-(2-thienyl)-2-propenimidate HCl in 3 ml. of ethanol, 0.6 g. of triethylamine and 0.252 g. of cyanamide are added successively. After stirring at room temperature for 30 minutes, the solvent is removed under reduced pressure. To the residue, ethyl acetate and water are added. The ethyl acetate layer is worked up in the usual manner.

Step B—The residue from the ethyl acetate layer of Step A is dissolved in MeOH by warming and after adding 12 ml. of methylamine solution (40% in methanol), the mixture is allowed to stand overnight. The precipitate is collected and recrystallized from ethanol-ether (1:1) a compound of the formula:

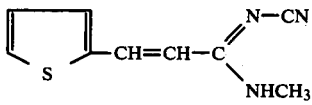

which has the following characteristics is obtained:
mp: 182°–184° C.
ir: 3400, 3220, 2150, 1620, 1580, 1400 cm.$^{-1}$
M.S.: m/e 191 (M+)

EXAMPLE 4

Compound 4:
N-n-Propyl-N'-cyano-3-(2-furyl)-2-propenimidamide

Ethyl 3-(2-furyl)-2-propenimidate HCl in an amount of 1.34 g. is dissolved in 3 ml. of ethanol and then an equimolar amount of triethylamine is added to the ice-cooled resulting solution. To this solution, cyanamide (0.25 g.) is added and stirring is continued for 1 hour at room temperature. After removal of solvent from the mixture, the resulting residue is dissolved in ethyl acetate. The ethyl acetate layer is washed with water and dried with MgSO4. To the residue, after removal of ethyl acetate, MeOH (3 ml.) and n-butylamine (1.1 g.) are added with slight warming and stirring is continued for 1 hour. The mixture is evaporated and resulting residue is submitted to column chromatography (KIESEL GEL 40 Ⓣ: ethyl acetate for eluent). The thus obtained crystals, which are recrystallized from acetone have the formula:

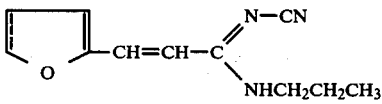

and the following characteristics:
mp. 188°–189° C.
ir. 3320, 3150, 2150, 1640, 1450 cm.$^{-1}$
M.S.: m/e 217 (M+)

EXAMPLE 5

Compound 35:
N-Isopropyl-N'-carbamoyl-3-(2-thienyl)-2-propenimidamide HCl.

HCl gas is bubbled through a solution of compound 5, i.e. N-isopropyl-N'-cyano-3-(2-thienyl)-2-propenimidamide (0.05 g.) in ethanol (7 ml.) for one hour under stirring. Ethanol is removed under reduced pressure to approximately one half volume. By adding ether to the mixture, a precipitate of the product is formed of the formula

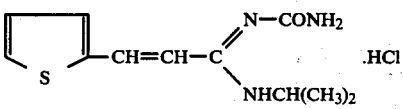

mp: 161°–3° C.
ir: 3400, 3150, 1710, 1640, 1600, 1570, 1270 cm.$^{-1}$

M.S.: m/e 237 (M+ - HCl)

EXAMPLE 6

When in the procedure of Example 3, Step A, one of the following compounds:
Ethyl 3-(2-thienyl)-2-propenimidate HCl,
Ethyl 3-(2-furyl)-2-propenimidate HCl or,
Ethyl 3-phenyl-2-propenimidate HCl is reacted with cyanamide and then a corresponding amine in the procedure of Example 3, Step B, compounds having the following structure and characteristics are obtained.

Compound 6:
N-Ethyl-N'-cyano-3-(2-furyl)-2-propenimidamide

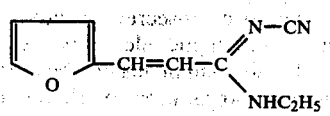

mp: 137°–8° C.
ir: 3240, 3100, 2930–80, 2170, 1640, 1590, 1570, 1530, 1300, 1210 cm.$^{-1}$
M.S.: m/e 189 (M+)

Compound 10:
N-Propionylamino-N'-cyano-3-(2-furyl)-2-propenimidamide

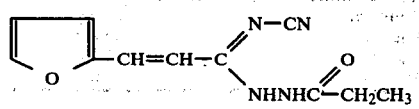

mp: 97°–102° C.
ir: 3320, 3170, 2150, 1660, 1620, 1580, 1530, 1375 cm.$^{-1}$
M.S.: m/e 216 (M+)

Compound 11:
N-n-Propyl-N'-cyano-3-phenyl-2-propenimidamide

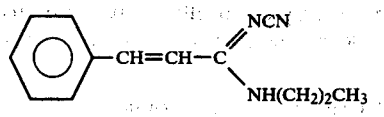

MP: 135°–6°
ir: 3230, 3100, 2950, 2160, 1640, 1580, 1540 cm.$^{-1}$
M.S. m/e 213 (M+)

Compound 12:
N-n-Butyl-N'-cyano-3-phenyl-2-propenimidamide

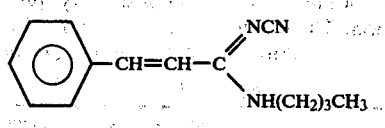

mp: 176°–8°
ir: 3325, 3250, 3160, 2960, 2160, 1660, 1640, 1585 cm.$^{-1}$
M.S.: m/e 227 (M+)

Compound 13:
N-Isopropyl-N'-cyano-3-phenyl-2-propenimidamide

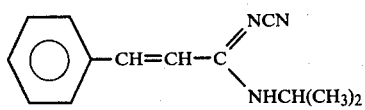

mp: 197°–200°
ir: 3250, 3100, 2960, 2160, 1640, 1590, 1540 cm$^{-1}$
M.S. m/e 213 (M$^+$)

Compound 14:
N-Ethyl-N'-cyano-3-phenyl-2-propenimiidamide

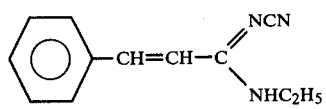

mp: 142°–5°
ir: 3240, 3100, 2960, 2160, 1640, 1590 cm$^{-1}$
M.S.: m/e 199 (M$^+$)

Compound 15:
N-Isobutyl-N'-cyano-3-phenyl-2-propenimidamide

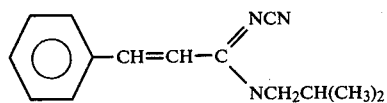

mp: 143°–6°
ir: 3240, 3100, 2940, 2150, 1635, 1580 cm$^{-1}$
M.S.: m/e 227 (M$^+$)

Compound 16:
N-Cyclohexyl-N'-cyano-3-phenyl-2-propenimidamide

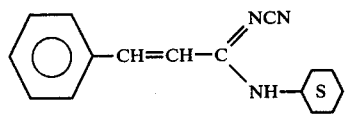

mp: 163°–6° C.
ir: 3230, 2820, 2160, 1660, 1640, 1580, 1540 cm$^{-1}$
M.S.: m/e 254 (M$^+$)

Compound 17: N-(3-Methylcyclohexyl)-N'-cyano-3-(2-furyl)-2-propenimidamide

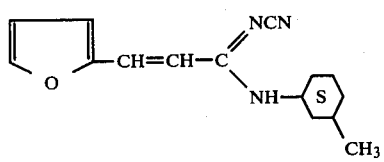

mp: 184°–8° C.
ir: 3340, 3170, 2160, 1660, 1535, 1450, 1385, 1260 cm$^{-1}$
M.S.: m/e 257 (M$^+$)

Compound 18:
N-Phenethyl-N'-cyano-3-(2-furyl)-2-propenimidamide

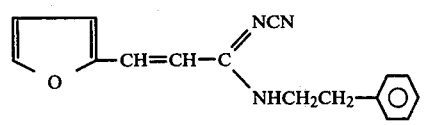

mp: 124°–7°
ir: 3210, 3170, 3140, 2910, 2160, 1640, 1560, 1520, 1460 cm$^{-1}$
M.S.: m/e 265 (M$^+$)

Compound 19: N-Isopropyl-N'-cyano-3-(2-furyl)-2(E)-propenimidamide

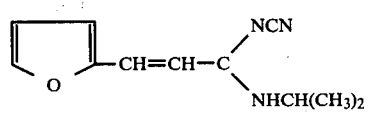

mp: 135°–7°
ir: 3320, 3160, 2950, 2150, 1640, 1560 cm$^{-1}$
M.S.: m/e 203 (M$^+$)

Compound 20:
N-Methyl-N'-cyano-3-phenyl-2-propenimidamide

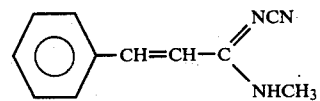

mp: 175°–9°
ir: 3230, 3100, 2160, 1640, 1595, 1540 cm$^{-1}$
M.S.: m/e 185 (M$^+$)

Compound 21:
N'-Cyano-3-(2-furyl)-2(E)-propenimidamide

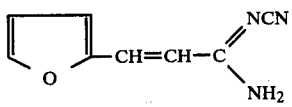

mp: 192°–4° C.
ir: 3320, 3170, 2160, 1655, 1530 cm$^{-1}$
M.S.: m/e 177 (M$^+$)

Compound 22: N-Isopropyl-N'-cyano-3-(2-furyl) 2(E)-propenimidamide

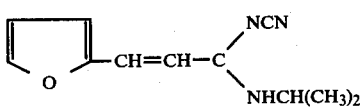

mp: 122°–4° C.
ir: 3240, 3080, 2950, 2150, 1630, 1540, 1520 cm$^{-1}$
M.S.: m/e 203 (M$^+$)

Compound 23:
N-(3-Methylcyclohexyl)-N'-cyano-3-phenyl-2-propenimidamide

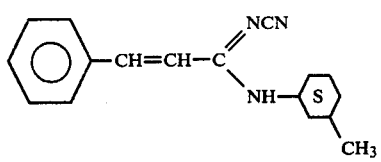

mp: 135°-8° C.
ir: 3210, 3075, 2900, 2150, 1660, 1630, 1575 cm$^{-1}$
M.S.: m/e 267 (M+)

Compound 24: N(4-Methylcyclohexyl) N'-cyano-3-phenyl-2-propenimidamide

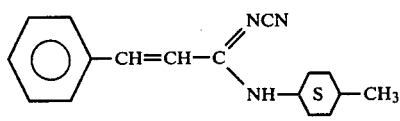

mp: 157°-9° C.
ir: 3200, 2150, 1660, 1640, 1570, 1535 cm$^{-1}$
M.S.: m/3 267 (M+)

EXAMPLE 7

By using respectively, Compound 2, 11, 12, 13, 16, 20, 23, 24 and 9 as the starting material in the procedure of Example 5, the following products are obtained.

Compound 26:
N'-Carbamoyl-3-(2-furyl)-2-propenimidamide hydrochloride

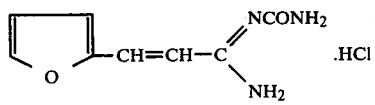

mp: 192°-4° C.
ir: 3240, 3150, 2920, 1725, 1660, 1630, 1520, 1470, 1380, 1320 cm$^{-1}$
M.S.: m/e 179 (M+-HCl)

Compound 27:
N-n-Propyl-N'-carbamoyl-3-phenyl-2-propenimidamide hydrochloride

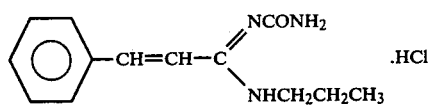

mp: 175°-8° C.
ir: 3230, 3110, 2950, 1720, 1650, 1610, 1570 cm$^{-1}$
M.S.: m/e 231 (M+-HCl)

Compound 28:
N-n-Butyl-N'-carbamoyl-3-phenyl-2-propenimidamide hydrochloride

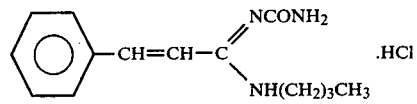

mp: 171°-4° C.
ir: 3210, 2950, 1715, 1650, 1600, 1560 cm$^{-1}$
M.S.: m/e 245 (M+-HCl)

Compound 29:
N-Isopropyl-N'-carbamoyl-3-phenyl-2-propenimidamide hydrochloride

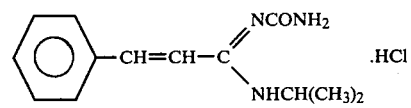

mp: 165°-6° C.
ir: 3250, 3150, 1710, 1640, 1600, 1560 cm$^{-1}$
M.S.: m/e 231 (M+-HCl)

Compound 30:
N-Cyclohexyl-N'-carbamoyl-3-phenyl-2-propenimidamide hydrochloride

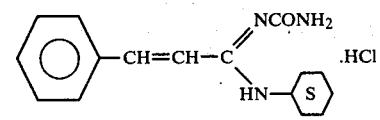

mp: 180°-3° C.
ir: 3250, 3120, 2900, 1720, 1640, 1600, 1560 cm$^{-1}$
M.S.: m/e 271 (M+-HCl)

Compound 31:
N-Methyl-N'-carbamoyl-3-phenyl-2-propenimidamide HCl

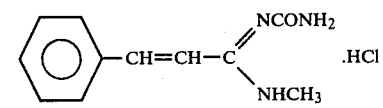

mp: 175°-8° C.
ir: 3250, 3130, 1780, 1660, 1610 cm$^{-1}$
M.S.: m/e 203 (M+-HCl)

Compound 32:
N-(3-Methylcyclohexyl)-N'-carbamoyl-3-phenyl-2-propenimidamide hydrochloride

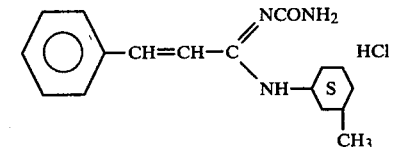

mp: 169°-172° C.
ir: 3280, 3100, 2910, 2850, 1730, 1650, 1600, 1460 cm$^{-1}$

M.S.: m/e 285 (M+-HCl)

Compound 33:
N-(4-Methylcyclohexyl)-N'-carbamoyl-3-phenyl-2-propenimidamide hydrochloride

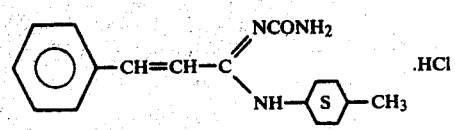

mp: 157°-9°
ir: 3200, 2150, 1660, 1640, 1570, 1535 cm$^{-1}$
M.S.: m/e 285 (M+-HCl)

Compound 34:
N-(4-Methylcyclohexyl)-N'-carbamoyl-3-(2-furyl)-2-propenimidamide hydrochloride

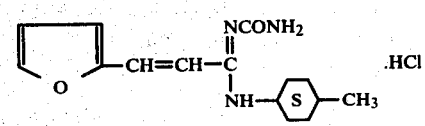

mp: 185°-192° C.
ir: 3380, 3270, 1720, 1640, cm$^{-1}$
M.S.: m/e 275 (M+-HCl)

EXAMPLE 8

Compound 38:
N-n-Propyl-N'-cyano-3-(o-chlorophenyl)-2-propenimidamide

Step A—Preparation of: Ethyl 3-(o-chlorophenyl)-2-propenimidate hydrochloride.

3-(o-Chlorophenyl)-2-propenenitrile in an amount of 10.47 g. is dissolved in a mixture of 10 ml. of ethanol and 5 ml. of ether. After 2.34 g. of HCl gas is added to the solution at 0°-3° C., the solution is allowed to stand for a week at room temperature. Then ether is added and the precipitated crystals are filtered; 7.44 g. of the desired imidate HCl are obtained.

Step B—To the solution of 2.416 g. of ethyl 3-(o-chlorophenyl)-2-propenimidate hydrochloride in 9 ml. of ethanol, 0.01 g. of triethylamine and 0.42 g. of cyanamide are added successively. After stirring at room temperature for 1 hour, the solvent is removed under reduced pressure. To the residue, ethyl acetate and water are added. The ethyl acetate layer is washed with water and dried over Na$_2$SO$_4$. After removal of the solvent by distillation, the residue is dissolved in 10 ml. of ethanol. To this solution 3 ml. of n-propylamine are added and the resulting mixture is allowed to stand overnight. After removal of solvent, the product is washed with ethylacetate-n-hexane (1:1). Recrystallization from ethanol gives Compound 38 of the formula:

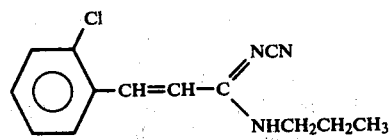

mp: 134°-6° C.
ir: (KBr) 3250, 2160, 1640, 1580, 1560, 1540 cm.$^{-1}$
M.S. m/e 247 (M+)

EXAMPLE 9

Compound 57:
N-Methyl-N'-carbamoyl-3-(o-chlorophenyl)-2-propenimidamide hydrochloride Ethyl 3-(o-chlorophenyl)-2-propenimidate hydrochloride obtained in Example 8, Step A; is reacted with methylamine in the same procedure as that of Example 8, Step B; 1.59 g. of the obtained N-methyl-N'-cyano-3-(o-chlorophenyl)-2-propenimidamide is added to 15 ml. of ethanol.

Then dry HCl gas is bubbled through the solution at 0°-5° C. for one hour. The resulting solution is allowed to stand overnight. After removal of ethanol by distillation, the residue is recrystallized from ethanol and 1.30 g. of the desired compound is obtained which has the formula:

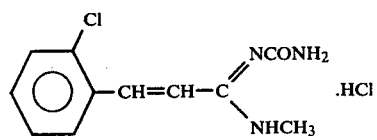

mp: 223°-8° C.
ir(KBr method): 3350, 3200, 3100, 2830, 1710, 1650, 1620 cm.$^{-1}$
M.S. m/s 237 (M+-HCl)

EXAMPLE 10

The following compounds are obtained by means of the same procedure as that of Example 8 or Example 9

Compound 36:
N-Methyl-N'-cyano-3-(o-chlorophenyl)-2-propenimidamide mp: 200°-201° C.
M.S. m/e 219 (M+)

Compound 37:
N-Ethyl-N'-cyano-3-(o-chlorophenyl)-2-propenimidamide mp: 186°-7° C.
M.S. m/e 233(M+)

Compound 39:
N-Isobutyl-N'-cyano-3-(o-chlorophenyl)-2-propenimidamide

M.P. 134°-6° C.
M.S. m/e 261 (M+)

Compound 40:
N-Cyclohexyl-N'-cyano-3-(o-chlorophenyl)-2-propenimidamide mp: 166°-8° C.
M.S. m/e 288 (M+)

Compound 41:
N-(4-Methycyclohexyl)-N'-cyano-3-(o-chlorophenyl)-2-propenimidamide mp: 164°-6° C.
M.S. m/e 301 (M+)

Compound 42:
N-Isopropyl-N'-cyano-3-(o-chlorophenyl)-2-propenimidamide mp: 144°-6° C.

M.S. m/e 247 (M+)

Compound 43:
N-Ethyl-N'-cyano-3-(p-chlorophenyl)-2-propenimidamide
mp: 180°-4° C.
M.S. m/e 233 (M+)

Compound 44:
N-Isopropyl-N'-cyano-3-(p-chlorophenyl)-2-propenimidamide
mp: 177°-181° C.
M.S. m/e 247 (M+)

Compound 45:
N-n-Propyl-N'-cyano-3-(p-chlorophenyl)-2-propenimidamide
mp: 161°-4° C.
M.S. m/e 247 (M+)

Compound 46:
N-Isobutyl-N'-cyano-3-(p-chlorophenyl)-2-propenimidamide
mp: 180°-5° C.
M.S. m/e 261 (M+)

Compound 47:
N-Cyclohexyl-N'-cyano-3-(p-chlorophenyl)-2-propenimidamide
mp: 210°-2° C.
M.S. m/e 287 (M+)

Compound 48:
N-(4-Methylcyclohexyl)-N'-cyano-3-(p-chlorophenyl)-2-propenimidamide
mp: 218°-220° C.
M.S. m/e 301 (M+)

Compound 49:
N-Methyl-N'-cyano-3-(p-methoxyphenyl)-2-propenimidamide
mp: 198°-200° C.
M.S. m/e 215 (M+)

Compound 50:
N-Ethyl-N'-cyano-3-(p-methoxyphenyl)-2-propenimidamide
mp: 156°-160° C.
M.S. m/e 299 (M+)

Compound 51:
N-n-Propyl-N'-cyano-3-(p-methoxyphenyl)-2-propenimidamide
mp: 134°-140° C.
M.S. m/e 243 (M+)

Compound 52:
N-Isopropyl-N'-cyano-3-(p-methoxyphenyl)-2-propenimidamides
mp: 138°-143° C.
M.S. m/e 243 (M+)

Compound 53:
N-Isobutyl-N'-cyano-3-(p-methoxyphenyl)-2-propenimidamide
mp: 140°-144° C.
M.S. m/e 257 (M+)

Compound 54:
N-Cyclohexyl-N'-cyano-3-(p-methoxyphenyl)-2-propenimidamide
mp: 140°-146° C.
M.S. m/e 283 (M+)

Compound 55:
N-(4-Methylcyclohexyl)-N'-cyano-3-(p-methoxyphenyl)-2-propenimidamide
mp: 158°-160° C.
M.S. m/e 297 (M+)

Compound 56:
N-Isopropyl-N'-carbamoyl-3-(o-chlorophenyl)-2-propenimidamide hydrochloride
mp: 177°-8° C.
M.S. m/e 265 (M+-HCl)

Compound 58:
N-Ethyl-N'-carbamoyl-3-(o-chlorophenyl)-2-propenimidamide hydrochloride
mp: 175°-178° C.
M.S. 251 (M+-HCl)

Compound 59:
N-Cyclohexyl-N'-carbamoyl-3-(o-chlorophenyl)-2-propenimidamide hydrochloride
mp: 277°-9° C.
M.S. m/e 306 (M+-HCl)

Compound 60:
N-n-Propyl-N'-carbamoyl-3-(o-chlorophenyl)-2-propenimidamide hydrochloride
mp: 165°-9° C.
M.S. m/e 265 (M+-HCl)

Compound 61:
N-(4-Methylcyclohexyl)-N'-carbamoyl-3-(o-chlorophenyl)-2-propenimidamide hydrochloride
mp: 210°-220° C.
M.S. m/e 319 (M+-HCl)

Compound 62:
N-Isopropyl-N'-carbamoyl-3-(p-chlorophenyl)-2-propenimidamide hydrochloride
mp: 135°-7° C.
M.S. m/e 302 (M+-HCl)

Compound 63:
N-Cyclohexyl-N'-carbamoyl-3-(p-chlorophenyl)-2-propenimidamide hydrochloride
mp: 144°-6° C.
M.S. m/e 342 (M+-HCl)

Compound 64:
N-(4-Methylcyclohexyl)-N'-carbamoyl-3-(p-chlorophenyl)-2-propenimidamide hydrochloride
mp: 127°-9° C.
M.S. m/e 319 (M+-HCl)

Compound 65:
N-Isopropyl-N'-carbamoyl-3-(p-methoxyphenyl)-2-propenimidamide hydrochloride
mp: 160°-175° C.
M.S. m/e 261 (M+-HCl)

Compound 66:
N-Cyclohexyl-N'-carbamoyl-3-(p-methoxyphenyl)-2-propenimidamide hydrochloride mp: 130°–135° C.
M.S. m/e 301 (M+-HCl)

Compound 67:
N-(4-Methylcyclohexyl)-N'-carbamoyl-3-(p-methoxyphenyl)-2-propenimidamide hydrochloride mp: 175°–180° C.
M.S. m/e 315 (M+-HCl)

What we desire to protect and claim by Letters Patent is:

1. A compound of the formula:

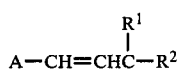

wherein:
A is a furyl, thienyl, phenyl, chlorophenyl or lower-alkoxyphenyl group;
$R^1$ represents =NCN or =NCONH$_2$ and
$R^2$ represents —NHR$^3$ or —NHNHCOR$^4$, wherein $R^3$ is a hydrogen atom, or a lower-alkyl, phen-lower-alkyl or cyclohexyl group, said cyclohexyl group being optionally substituted by lower-alkyl and $R^4$ is a lower alkyl group, and
pharmaceutically acceptable acid addition salts thereof.

2. A compound according to claim 1 wherein
A is a furyl, thienyl, phenyl, chlorophenyl or methoxyphenyl group;
$R^1$ represents =NCN or =NCONH$_2$ and
$R^3$ represents —NHR$^3$ or —NHNHCOC$_2$H$_5$, wherein $R^3$ is a hydrogen atom, or an alkyl group containing 1 to 4 carbon atoms, a phenethyl group or a cyclohexyl group optionally substituted by a lower alkyl group.

3. A compound as defined in claim 1 which is pharmaceutically acceptable acid addition salt.

4. A compound according to claim 1 in which A is a furyl group.

5. A compound according to claim 1 in which A is a thienyl group.

6. A compound according to claim 1 in which A is a phenyl chlorophenyl or lower-alkoxy-phenyl group.

7. A compound according to one of claims 1 to 6 in which $R^1$ represents =NCN.

8. A compound according to one of claims 1 to 6 in which $R^1$ represents =NCONH$_2$.

9. A compound according to claim 7 in which $R^2$ represents —NHR$^3$.

10. A compound according to claim 8 in which $R^2$ represents —NHR$^3$.

11. A compound according to claim 7 in which $R^2$ represents —NHNHCOR$^4$.

12. A compound according to claim 8 in which $R^2$ represents —NHNHCOR$^4$.

13. A therapeutic composition to inhibit gastric juice secretion comprising a pharmaceutically acceptable carrier and as an active ingredient a compound defined in claim 1 in an amount effective to inhibit gastric juice secretion.

* * * * *